United States Patent
Miyake et al.

(10) Patent No.: US 10,226,199 B2
(45) Date of Patent: Mar. 12, 2019

(54) MEDICAL-IMAGE PROCESSING APPARATUS, METHOD FOR CONTROLLING THE SAME, AND STORAGE MEDIUM

(71) Applicant: CANON KABUSHIKI KAISHA, Tokyo (JP)

(72) Inventors: Noriaki Miyake, Kitakyushu (JP); Tsuyoshi Sakamoto, Kitakyushu (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/382,298

(22) Filed: Dec. 16, 2016

(65) Prior Publication Data
US 2017/0172383 A1   Jun. 22, 2017

(30) Foreign Application Priority Data

Dec. 21, 2015   (JP) ................................. 2015-248287
Dec. 21, 2015   (JP) ................................. 2015-248983

(51) Int. Cl.
*G06T 7/00*   (2017.01)
*A61B 5/00*   (2006.01)
(Continued)

(52) U.S. Cl.
CPC .......... *A61B 5/066* (2013.01); *A61B 1/00009* (2013.01); *A61B 1/00045* (2013.01);
(Continued)

(58) Field of Classification Search
CPC ..... G06T 7/0012; G06T 15/205; G06T 19/20; G06T 2207/10081; G06T 2207/30061;
(Continued)

(56) References Cited

U.S. PATENT DOCUMENTS 7,517,320 B2 * 4/2009 Wibowo ............ A61B 5/02007
                                                      600/529
7,646,903 B2 * 1/2010 Kaftan ................. G06K 9/6206
                                                      341/79
(Continued)

FOREIGN PATENT DOCUMENTS

JP     2011-135937 A     7/2011

OTHER PUBLICATIONS

Geiger et al. "Virtual bronchoscopy of peripheral nodules using arteries as surrogate pathways." Medical Imaging 2005: Physiology, Function, and Structure from Medical Images. vol. 5746. International Society for Optics and Photonics, 2005.*

(Continued)

*Primary Examiner* — Katrina R Fujita
(74) *Attorney, Agent, or Firm* — Canon U.S.A., Inc. IP Division

(57) ABSTRACT

An information processing apparatus includes an acquisition unit, a specification unit, a determination unit, a generation unit, and a display control unit. The acquisition unit acquires a three-dimensional image containing at least a tubular structure. The specification unit specifies a first point inside the tubular structure and specifies a lesion outside the tubular structure in the three-dimensional image. The determination unit determines whether a blood vessel is present in a region between the first point and the lesion based on signal values of voxels of the three-dimensional image in the region between the first point and the lesion. The generation unit generates a two-dimensional image of the tubular structure viewed from the first point based on the three-dimensional image. The display control unit displays information indicating a region of the lesion on the two-dimensional image to be distinguishable in determining whether a blood vessel is present in the region.

25 Claims, 8 Drawing Sheets

(51) Int. Cl.
| | |
|---|---|
| A61B 5/06 | (2006.01) |
| G06T 15/20 | (2011.01) |
| A61B 1/00 | (2006.01) |
| A61B 1/267 | (2006.01) |
| A61B 6/00 | (2006.01) |
| G06T 3/00 | (2006.01) |
| G06T 19/20 | (2011.01) |
| A61B 6/03 | (2006.01) |
| A61B 6/12 | (2006.01) |
| G06T 19/00 | (2011.01) |
| A61B 90/00 | (2016.01) |

(52) U.S. Cl.
CPC ........... *A61B 1/2676* (2013.01); *A61B 5/489* (2013.01); *A61B 5/743* (2013.01); *A61B 6/00* (2013.01); *A61B 6/032* (2013.01); *A61B 6/12* (2013.01); *A61B 6/466* (2013.01); *A61B 6/468* (2013.01); *A61B 6/50* (2013.01); *A61B 6/504* (2013.01); *G06T 3/0031* (2013.01); *G06T 7/0012* (2013.01); *G06T 15/205* (2013.01); *G06T 19/003* (2013.01); *G06T 19/20* (2013.01); *A61B 6/5217* (2013.01); *A61B 2090/3762* (2016.02); *A61B 2576/02* (2013.01); *G06T 2207/10081* (2013.01); *G06T 2207/30061* (2013.01); *G06T 2207/30064* (2013.01); *G06T 2207/30101* (2013.01); *G06T 2207/30172* (2013.01); *G06T 2210/41* (2013.01); *G06T 2219/004* (2013.01); *G06T 2219/2012* (2013.01)

(58) Field of Classification Search
CPC ... G06T 2207/30064; G06T 2219/2012; A61B 1/00009; A61B 1/00045; A61B 1/2676; A61B 5/066; A61B 5/489; A61B 5/743; A61B 6/00; A61B 2576/02
See application file for complete search history.

(56) References Cited

U.S. PATENT DOCUMENTS

| | | | | |
|---|---|---|---|---|
| 7,970,189 | B2* | 6/2011 | Buelow | G06T 7/155 382/128 |
| 9,037,215 | B2* | 5/2015 | Higgins | G06T 19/003 382/128 |
| 2005/0107679 | A1* | 5/2005 | Geiger | G06T 19/003 600/407 |
| 2005/0182295 | A1* | 8/2005 | Soper | A61B 1/0008 600/117 |
| 2007/0092864 | A1* | 4/2007 | Reinhardt | G06T 7/0012 435/4 |
| 2007/0286469 | A1* | 12/2007 | Yamagata | G06T 7/0012 382/131 |
| 2008/0170771 | A1* | 7/2008 | Yamagata | G06F 19/321 382/128 |
| 2008/0298666 | A1* | 12/2008 | Mysore Siddu | G06T 7/0012 382/132 |
| 2011/0311124 | A1* | 12/2011 | Ohnishi | G06T 7/0012 382/134 |
| 2012/0123239 | A1* | 5/2012 | Han | A61B 5/08 600/407 |
| 2015/0012011 | A1* | 1/2015 | Trovato | A61B 17/3421 606/130 |
| 2015/0029184 | A1* | 1/2015 | Masumoto | G06T 19/00 345/419 |
| 2017/0084027 | A1* | 3/2017 | Mintz | G06T 7/248 |

OTHER PUBLICATIONS

Gibbs et al. "3D path planning and extension for endoscopic guidance." Medical Imaging 2007: Visualization and Image-Guided Procedures. vol. 6509. International Society for Optics and Photonics, 2007.*

Lou et al. "Object-based deformation technique for 3D CT lung nodule detection." Medical Imaging 1999: Image Processing. vol. 3661. International Society for Optics and Photonics, 1999.*

* cited by examiner

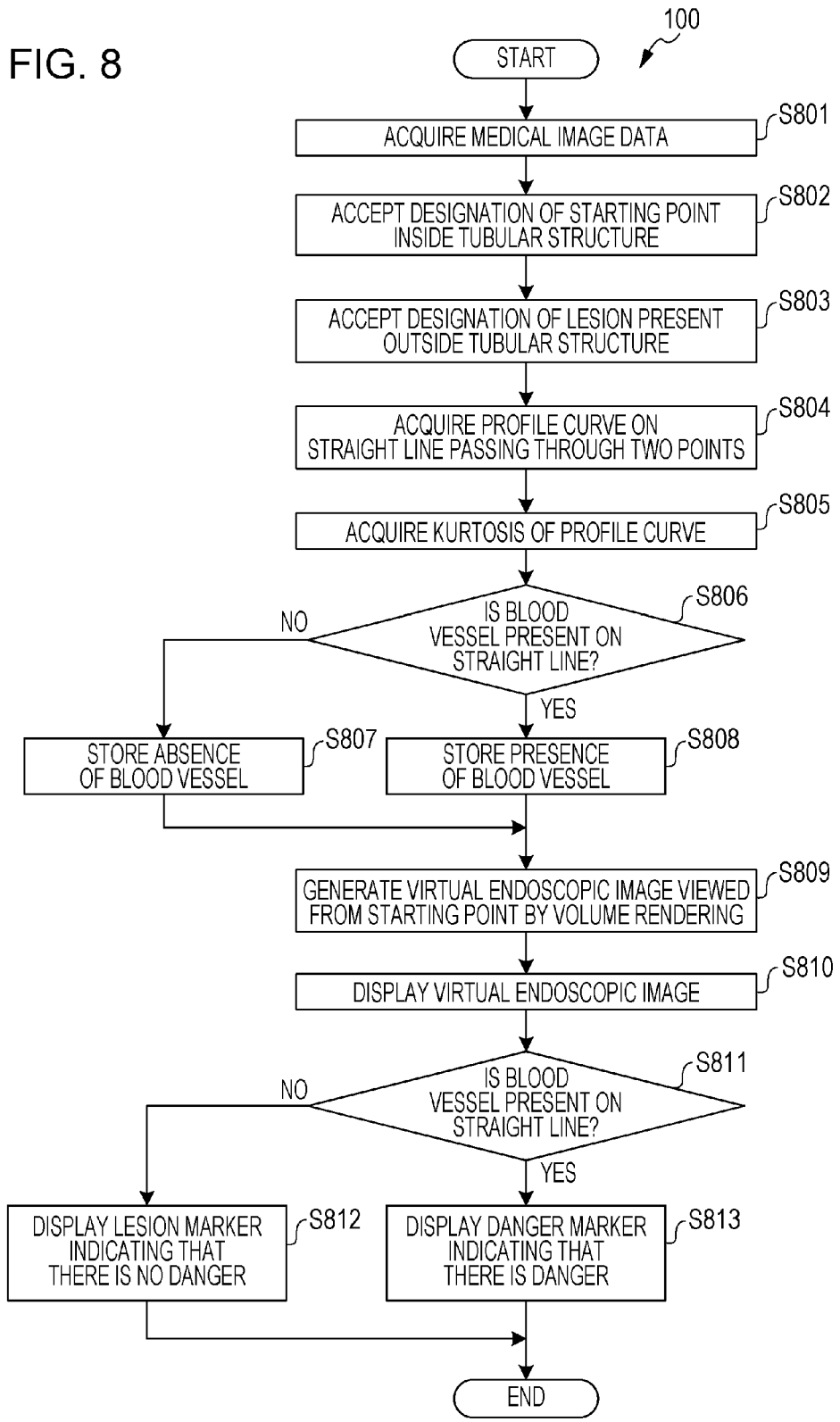

MEDICAL-IMAGE PROCESSING APPARATUS, METHOD FOR CONTROLLING THE SAME, AND STORAGE MEDIUM

BACKGROUND OF THE INVENTION

Field of the Invention

The present disclosure relates to a medical-image processing apparatus capable of determining whether a blood vessel is present outside a tubular structure, a method for controlling the same, and a storage medium.

Description of the Related Art

A blood vessel is a tubular structure, such as a vein, artery, or capillary, that carries blood through tissues and organs. A lesion is an abnormal damage or change in tissue of an organism, usually caused by disease or trauma. Doctors sometimes extract tissue from a lesion (a target) of a patient to perform pathological inspection or the like.

Specifically, doctors acquire the tissue of a lesion outside a tubular structure, such as a bronchial tube, (for example, a lung region serving as an airway in a respiratory tract that conducts air into the lungs) of a patient by inserting an injection needle into the tubular structure.

In inserting a needle into the target from the interior of a tubular structure, sticking the needle into a blood vessel by mistake will pose a danger to the patient. To prevent it, doctors need to insert the needle away from a blood vessel present outside the tubular structure.

Japanese Patent Laid-Open No. 2011-135937 discloses a technique for forming a three-dimensional image in which a virtual three-dimensional image of the actual motion of a surgical tool is combined with an image of a body organ and so forth based on a tomographic image acquired by an X-ray computed tomography (CT) scanner or a nuclear magnetic resonance imaging (MRI) scanner.

However, this is troublesome because doctors need to form an image of the inner wall of the tubular structure and an image of blood vessels running outside the tubular structure and to check the images in order to determine how the blood vessels run outside the tubular structure.

SUMMARY OF THE INVENTION

According to an aspect of the present disclosure, an information processing apparatus includes an acquisition unit configured to acquire a three-dimensional image containing at least a tubular structure, a specification unit configured to specify a first point inside the tubular structure and specify a lesion outside the tubular structure in the three-dimensional image, a determination unit configured to determine whether a blood vessel is present in a region between the first point and the lesion based on signal values of voxels of the three-dimensional image in the region between the first point and the lesion, a generation unit configured to generate a two-dimensional image of the tubular structure viewed from the first point based on the three-dimensional image, and a display control unit configured to display information indicating a region of the lesion on the two-dimensional image to be distinguishable in a result of determining whether a blood vessel is present in the region.

Further features of the present invention will become apparent from the following description of exemplary embodiments with reference to the attached drawings.

BRIEF DESCRIPTION OF THE DRAWINGS

FIG. 8 is a flowchart illustrating the details of a process in a second embodiment of the present disclosure.

DESCRIPTION OF THE EMBODIMENTS

Embodiments of the present disclosure will be described hereinbelow with reference to the attached drawings. The embodiments described below are specific examples of the present disclosure and specific examples of the configuration described in the claims.

First Embodiment

This embodiment is an example of an image processing apparatus that generates a two-dimensional image of a model viewed from a viewpoint inside a tubular structure based on volume data generated from an X-ray computed tomographic image (a medical image) acquired by an X-ray computed tomography scanner (a medical-image diagnostic unit that produces cross-sectional images) by projection centered on the viewpoint. In displaying the two-dimensional image, if a blood vessel is present between a lesion outside a tubular structure and the position of the viewpoint, the user is notified of the presence of the blood vessel. The X-ray CT image is given for mere illustration, and any other image of the state of internal organs, such as those in a body that are self-contained or have a specific function, acquired by another modality, such as a magnetic resonance imaging (MRI) scanner, can be used.

Figure 1:
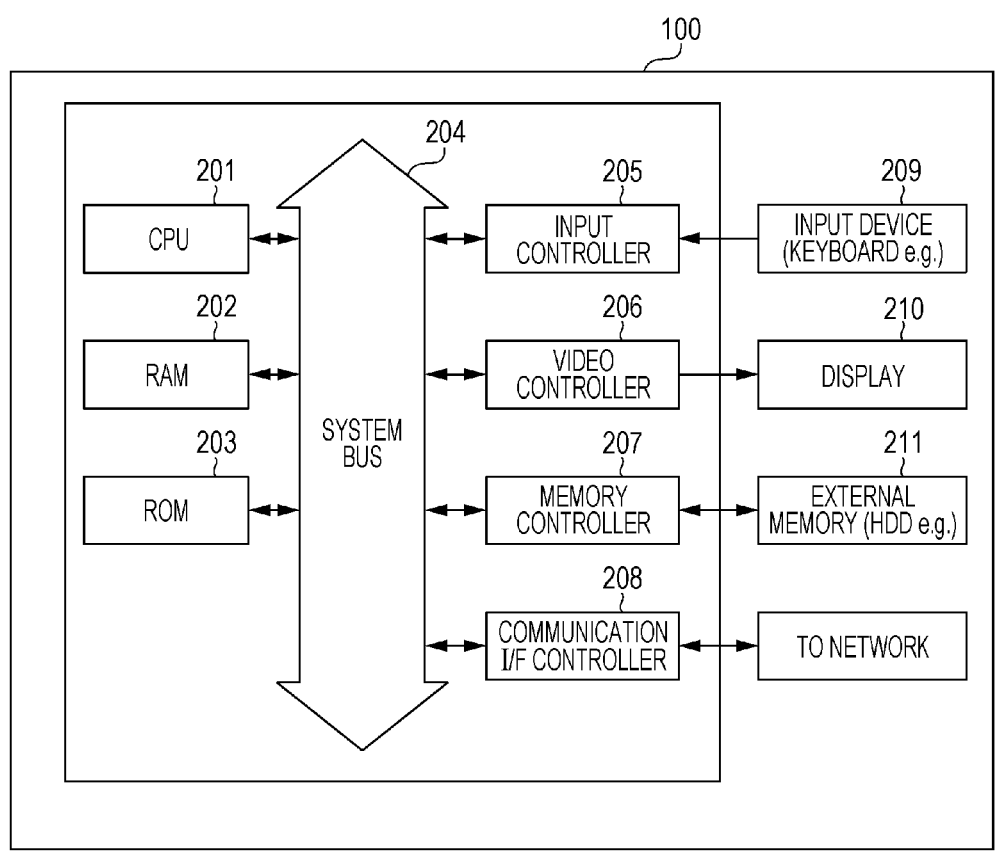
FIG. 1 is a diagram illustrating an example of the hardware configuration of a medical-image processing apparatus according to a first embodiment of the present disclosure.

First, an example of the hardware configuration of a medical-image processing apparatus 100 according to this embodiment will be described with reference to a block diagram in FIG. 1. When information is a medical image, the medical-image processing apparatus 100 may be thought of as an information processing apparatus.

A central processing unit (CPU) 201 controls the operation of the entire medical-image processing apparatus 100 and executes or controls processes that the medical-image processing apparatus 100 performs by executing the processes using computer programs and data stored in a random-access memory (RAM) 202 and a read-only memory (ROM) 203.

The RAM 202 has an area for storing computer programs and data loaded from an external memory 211 and data received from the outside via a communication (interface) I/F controller 208. The RAM 202 also has a work area for use in executing the various processes that the CPU 201 executes. Thus, the RAM 202 can provide various areas as appropriate.

The ROM 203 stores set data of the medical-image processing apparatus 100 that needs no rewriting and computer programs of the medical-image processing apparatus 100 that need no rewriting.

An input controller 205 is used to notify the CPU 201 of input from an input device 209. The input device 209 is a user interface including a keyboard and a mouse, which allows the user to input various instructions to the CPU 201.

A video controller 206 controls the display of the display 210. The display 210 is an example of a display device, on which the result of processing using the CPU 201 can be displayed using images and characters. The input device 209 and the display 210 may be combined into a touch panel screen.

A memory controller 207 is used to control reading and writing computer programs and data from/to the external memory 211. The external memory 211 is a large-capacity information storage unit, such as a hard disk drive (HDD). The external memory 211 stores an operating system (OS) and computer programs and data for causing the CPU 201 to execute or control the processes to be performed by the medical-image processing apparatus 100. The data includes known information described later. The computer programs and data stored in the external memory 211 are loaded into the RAM 202 as appropriate according to the control of the CPU 201 and are used by the CPU 201.

The communication I/F controller 208 is used to control data communication with an external device.

The CPU 201, the RAM 202, the ROM 203, the input controller 205, the video controller 206, the memory controller 207, and the communication I/F controller 208 are connected to a system bus 204.

Next, the functional configuration of the medical-image processing apparatus 100 will be described with reference to FIG. 2. The medical-image processing apparatus 100 includes a specification unit 2001, a storage unit 2002, an acquisition unit 2003, a blood-vessel determining unit 2004, a display control unit 2005, a section specification unit 2006, a distribution-information acquisition unit 2007, and a lesion-position acquisition unit 2008. Coordinates of a point may include a number or a set of numbers representing a position of the point along a figure such as a line or curve. In the coordinates (x, y, z), for example, the first number in the sequence is the x-coordinate, the second number is the y-coordinate, and the third number is the z-coordinate. The specification unit 2001 specifies a point inside a tubular structure, which may include features such as being long, round, cylindrical, or hollow that may contribute to conveying/containing liquids or gases. The storage unit 2002 stores medical image data containing at least a tubular structure. The acquisition unit 2003 acquires a profile curve indicating the signal values of voxels (including values on a regular grid in three-dimensional space) on a straight line passing through the specified point. The blood-vessel determining unit 2004 determines whether a blood vessel is present on the straight line based on the acquired profile curve. The display control unit 2005 displays a two-dimensional image generated based on the medical image data. The section specification unit 2006 specifies a section of the profile curve that exceeds a threshold. The distribution-information acquisition unit 2007 acquires distribution information indicating the distribution of the profile curve. The lesion-position acquisition unit 2008 acquires the position of a lesion.

Figure 2:
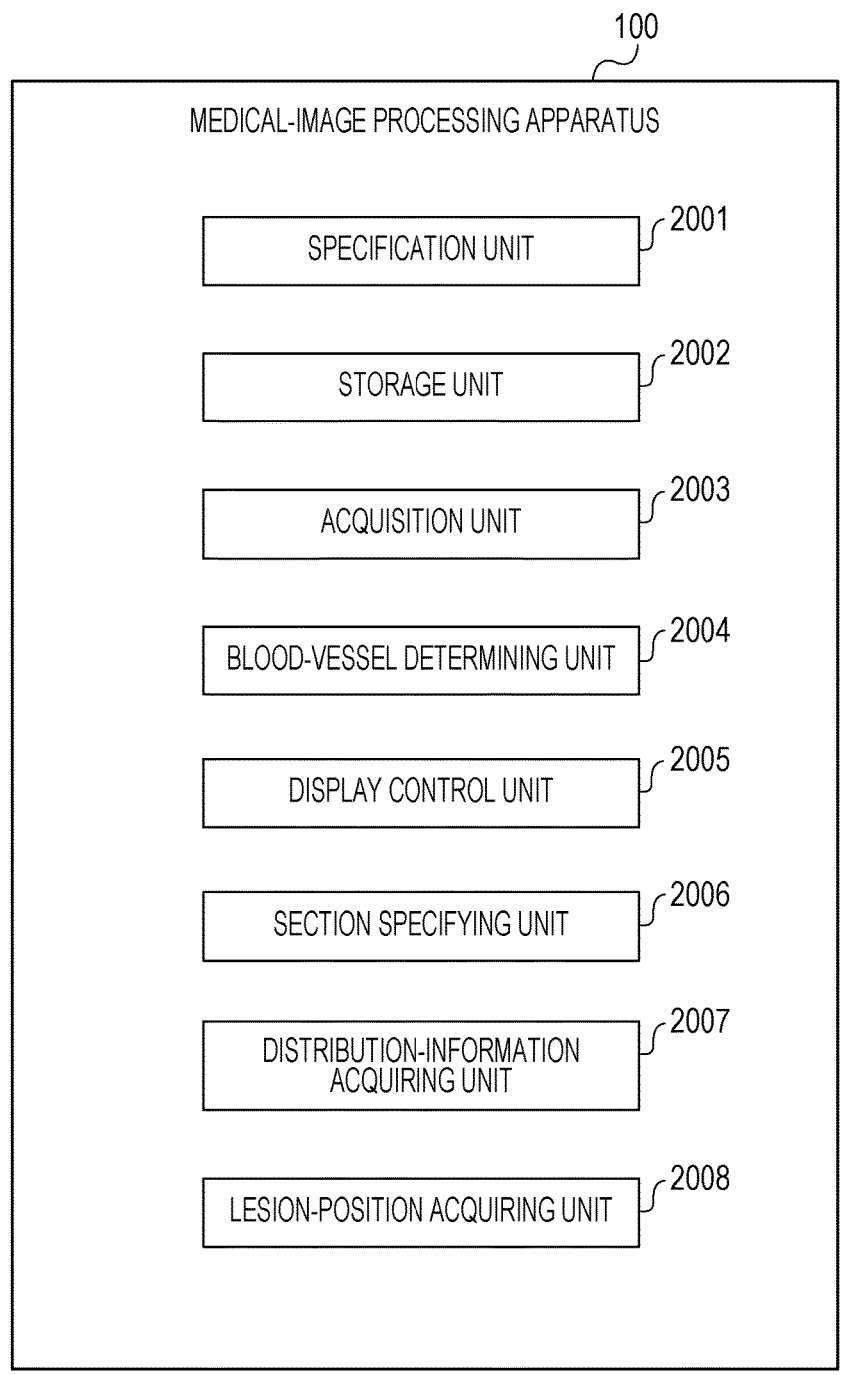
FIG. 2 is a diagram illustrating an example of the functional configuration of the medical-image processing apparatus according to the first embodiment.

That is descriptions of the functional configuration of the medical-image processing apparatus 100 shown in FIG. 2.

Figure 3:
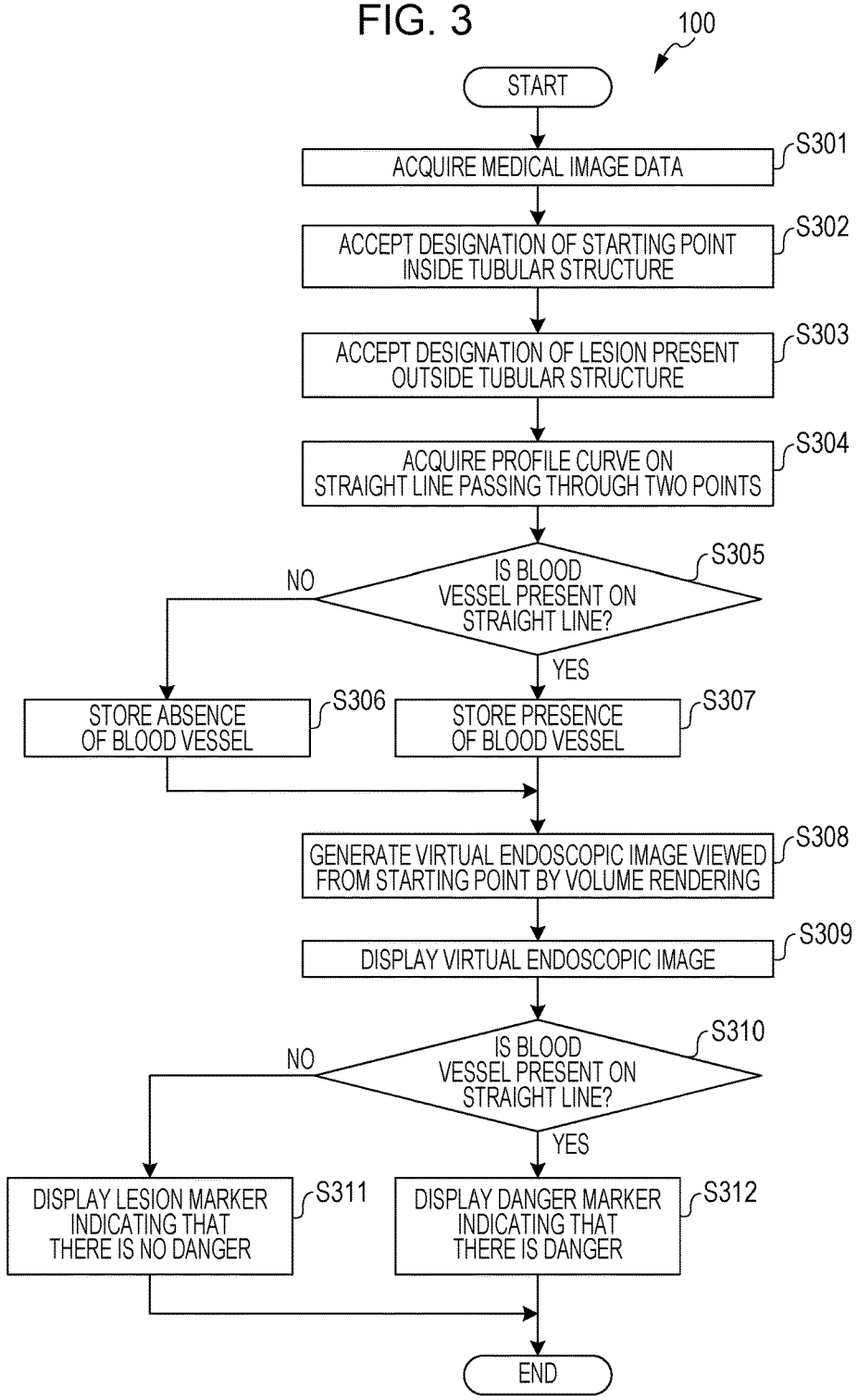
FIG. 3 is a flowchart illustrating the details of a process in the first embodiment.

Next, the operation (function) of the medical-image processing apparatus 100 will be described. In general, volume data on an object (a patient) can be generated from "a plurality of X-ray images of the whole or part of the object" acquired by an X-ray computed tomography (CT) scanner. As well known, the volume data is composed of voxels, in which each voxel is associated with a corresponding CT value (a signal value). In this embodiment, a virtual endoscopic image, which is a two-dimensional image of a model of the inner wall of a tubular structure (a bronchial tube) based on the volume data (an inner wall model), viewed from a designated viewpoint, is generated and displayed. The inner wall may include tissue layers. A process of generating the two-dimensional image of the inner wall model of the tubular structure using the medical-image processing apparatus 100 will be described with reference to the flowchart in FIG. 3. Although the flowchart in FIG. 3 is for a case in which the tubular structure is a bronchial tube, the flowchart in FIG. 3 can also be applied to a tubular structure other than the bronchial tube, for example, a stomach (which may include an internal organ where digestion of food occurs).

At step S301, the CPU 201 of the medical-image processing apparatus 100 acquires volume data (medical image data) and stores the data into the external memory 211 or the RAM 202. The source of the volume data is not limited to a specific source. For example, the volume data can be acquired from an external server or storage.

At step S302, the CPU 201 of the medical-image processing apparatus 100 sets a starting point (a viewpoint, corresponding to a first point) inside the bronchial tube for observing the inner wall model of the bronchial tube (corresponding to a specification unit). For example, the CPU 201 displays an image of the inner wall model of the bronchial tube or a tomographic image taken along a body axis on the display 210. The user can designate a desired position on the screen of the display 210 by operating the input controller 205 while observing the displayed image as a viewpoint position. Of course, the user can employ another viewpoint setting method or can designate a three-dimensional position of the viewpoint. In any case, the position of the viewpoint needs to be coordinates in the coordinate system of the volume data (or another coordinate system that can be converted to the above the coordinate system) in the bronchial tube, which may include a tube that carries air into tiny branches and smaller cells of the lungs after this air has passed through the mouth, nasal passages, or windpipe (trachea).

The CPU 201 stores the position of the starting point set by the user into the RAM 202 or the external memory 211. The starting point may be set without user operation; a preset position may be set as the starting point to be used below.

At step S303, the CPU 201 of the medical-image processing apparatus 100 receives designation of the point in a lesion outside the bronchial tube (for example, a lesion present in a lung region) (corresponding to the specification unit). For the designation of the point (position of the lesion, corresponding to a second point), the user may either receive the designation in advance or select a desired position on the screen of the display 210 and designate the position as the position of the lesion.

Figure 4:
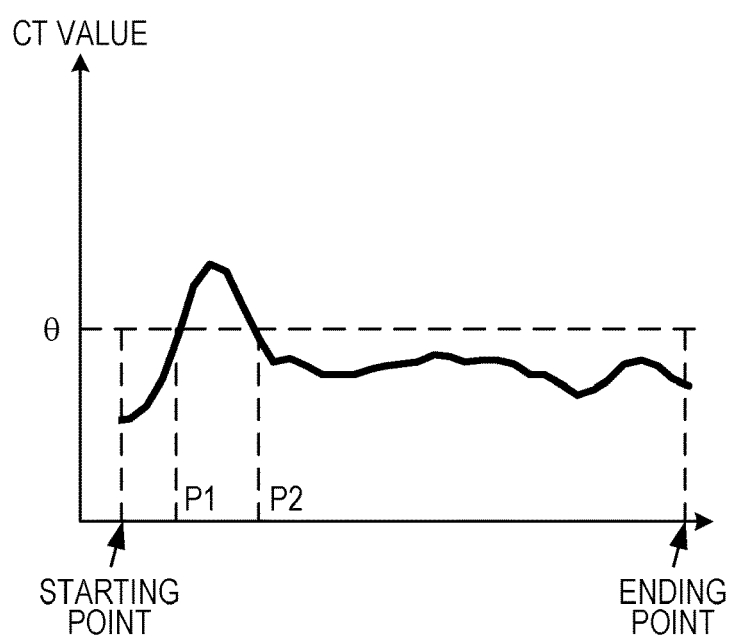
FIG. 4 is an example of a profile curve of CT values corresponding to voxels on a straight line when no blood vessel close to the wall of a tubular structure is present.
Figure 5:
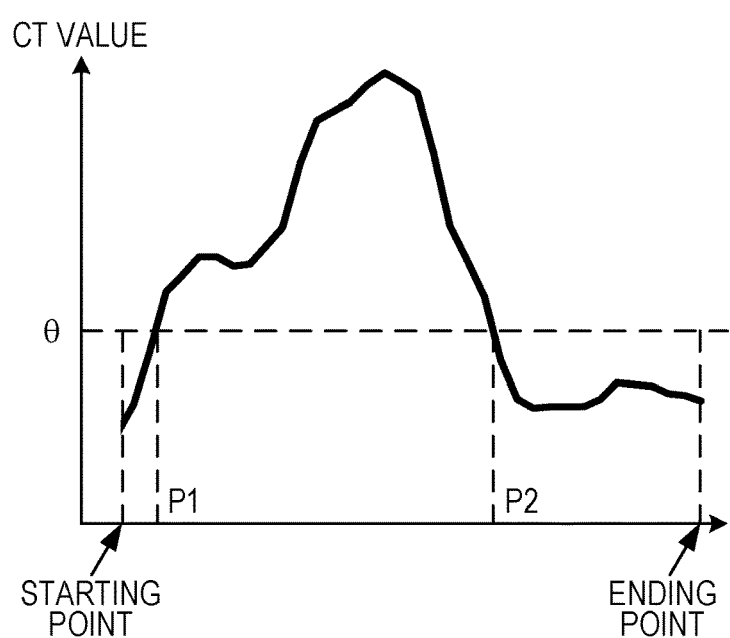
FIG. 5 is an example of a profile curve of CT values corresponding to voxels on a straight line when a blood vessel close to the wall of a tubular structure is present.

At step S304, the CPU 201 of the medical-image processing apparatus 100 acquires a profile curve, which is a graph in which CT values corresponding to voxels on a straight line starting from the position of the starting point designated at step S302 and passing an ending point at the position of the lesion designated at step S303 are placed in sequence (corresponding to an acquisition unit). Examples of the acquired profile curve are shown in FIGS. 4 and 5.

At step S305, the CPU 201 of the medical-image processing apparatus 100 determines whether a blood vessel is present outside the bronchial tube based on the shape of the profile curve acquired at step S304. This operation will be specifically described.

The operation will be described using the two profile curves shown in FIGS. 4 and 5 as examples of the profile curve acquired at step S304. The CPU 201 specifies a section in which CT values exceed a threshold θ (for example, −800 HU (Hounsfield units)) on the profile curve acquired at step S304. In FIGS. 4 and 5, the CT values exceed the threshold θ in the section from a position P1 (a position when the starting point is set at 0) to a position P2 (a position when the starting point is 0). In other words, this allows determination that the wall of the bronchial tube or a blood vessel is present between the starting point and the ending point of the straight line.

Here, whether only the inner wall of the bronchial tube is present or whether a blood vessel is present close to the bronchial tube can be determined from the distance of the section in which the CT values exceed the threshold θ (−800 HU), specifically, according to whether the following relations are satisfied:

$$B > k \times A$$

$$B \leq k \times A$$

where A is a distance from the starting point to the position P1, B is a distance from the starting point to the position P2, and k is an any constant, for example, approximately 3. If $B > k \times A$ (corresponding to a predetermined length) is satisfied, the CPU 201 determines that a blood vessel close to the wall of the bronchial tube is present in the section from the starting point to the ending point of the target straight line 470. If $B \leq k \times A$ is satisfied, the CPU 201 determines that a blood vessel close to the wall of the bronchial tube is not present in the section from the starting point to the ending point of the target straight line 470. According to this determination method, the profile curve shown FIG. 4 is an example of a profile curve when no blood vessel is present on the straight line. The profile curve shown in FIG. 5 is an example of a profile curve when a blood vessel is present on the straight line. In other words, the CPU 201 determines that a blood vessel is present based on the presence of a region of signal values corresponding to a blood vessel in the region between the first point and the second point. In another point of view, the CPU 201 determines whether a blood vessel is present in the region between the first point and the second point based on the signal values.

Figure 6A:
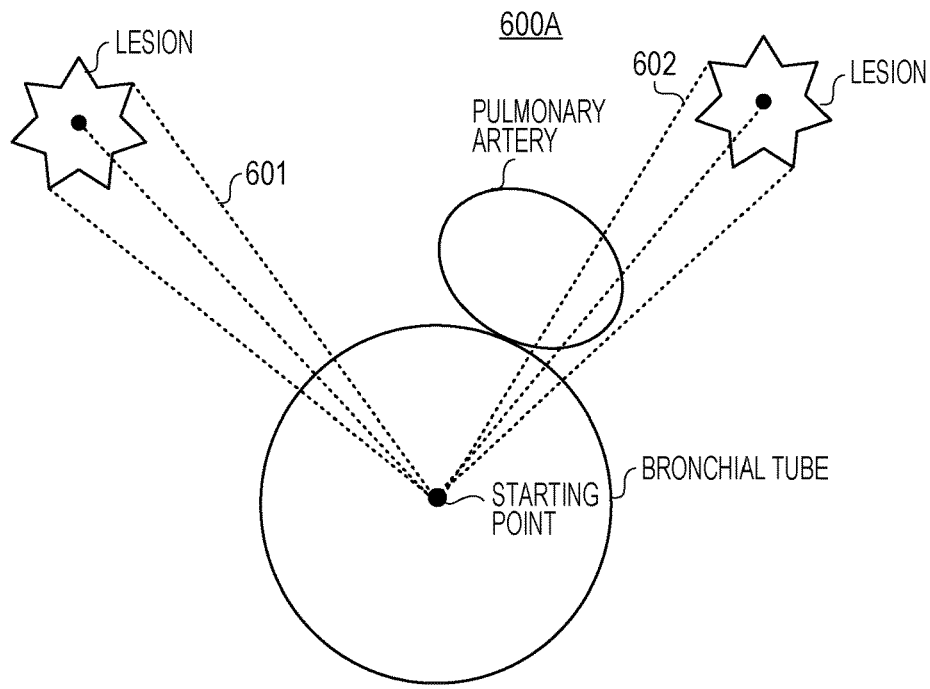
FIG. 6A is a diagram illustrating the positional relationship among a lesion, a bronchial tube, and a blood vessel when no blood vessel is present on a straight line.
Figure 6B:
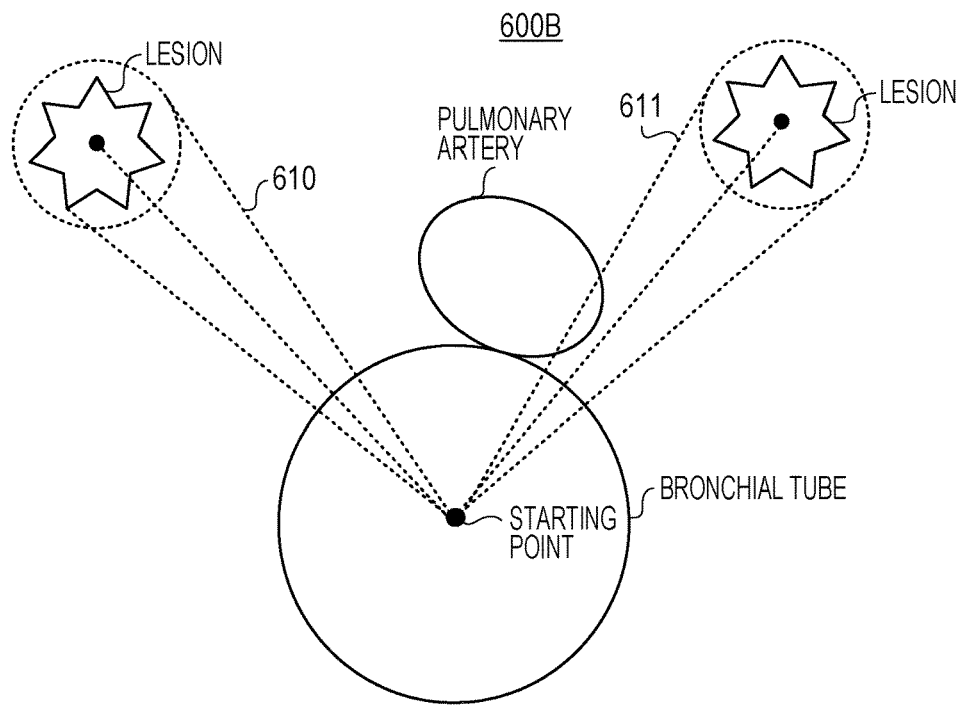
FIG. 6B is a diagram illustrating the positional relationship among a lesion, a bronchial tube, and a blood vessel when a blood vessel is present on a straight line.

An example of the positional relationship among a lesion (target), a bronchial tube, and a blood vessel is an image 600A illustrated in FIG. 6A. The image 600A is a conceptual diagram of a straight line 601 from a viewpoint inside the bronchial tube to the lesion, on which a blood vessel (a pulmonary artery) is not present, and a straight line 602 on which a blood vessel is present. With the straight line 601, the profile curve as shown in FIG. 4 is obtained. The shape of the profile curve shows that no blood vessel is present on the straight line. For the straight line 602, the profile curve as shown in FIG. 5 is obtained. This shows that a blood vessel is present. The profile curves shown in FIGS. 4 and 5 do not include a section corresponding to a lesion at which CT values sharply increase. Alternatively, it can be determined whether a blood vessel is present on a straight line containing a point on a virtual lesion region expanded by a predetermined amount and the starting point (the viewpoint), like an image 600B in FIG. 6B. In this case, since a straight line 611 in the image 600B contains a blood vessel, the user is notified of the presence of the blood vessel.

In this embodiment, the determination of whether a blood vessel is present on a straight line is performed using the profile curve of the straight line. Alternatively, the determination may be performed using a profile curve of a line segment between the starting point and the lesion.

It is needless to say that the above method is given for mere illustration and any method can be employed that allows determination of whether only the wall of the bronchial tube is present or a blood vessel close to the wall of the bronchial tube is present based on the shape of the profile curve.

If the result of the determination of presence of a blood vessel on a selected target straight line shows that a blood vessel close to the wall of the bronchial tube is not present, the process goes to step S306. If the result of the determination shows that a blood vessel close to the wall of the bronchial tube is present, the process goes to step S307.

At step S306, the CPU 201 of the medical-image processing apparatus 100 temporarily stores the fact that the profile curve acquired at step S304 indicates absence of a blood vessel in the RAM 202.

At step S307, the CPU 201 of the medical-image processing apparatus 100 temporarily stores the fact that the profile curve acquired at step S304 indicates presence of a blood vessel in the RAM 202.

At step S308, the CPU 201 of the medical-image processing apparatus 100 generates a virtual endoscopic image, which is a two-dimensional image of the inner wall model of the bronchial tube viewed from the starting point designated at step S302, using parameters by volume rendering, for example. Description of a technique for generating a virtual object image viewed from a viewpoint will be omitted because it is well known. For the color of the inner wall model, for example, colors defined by the parameters are assigned to the CT values of voxels corresponding to the inner wall of the bronchial tube.

At step S309, the CPU 201 of the medical-image processing apparatus 100 displays the virtual endoscopic image generated at step S308 on the display 210.

At step S310, the CPU 201 of the medical-image processing apparatus 100 determines whether a blood vessel is present on a straight line starting from the starting point designated at step S302 to an ending point, which is the position of the lesion designated at step S303, based on the information temporarily stored at step S306 or step S307. If the CPU 201 determines that no blood vessel is present, the process goes to step S311, and if the CPU 201 determines that a blood vessel is present, the process goes to step S312.

Figure 7A:
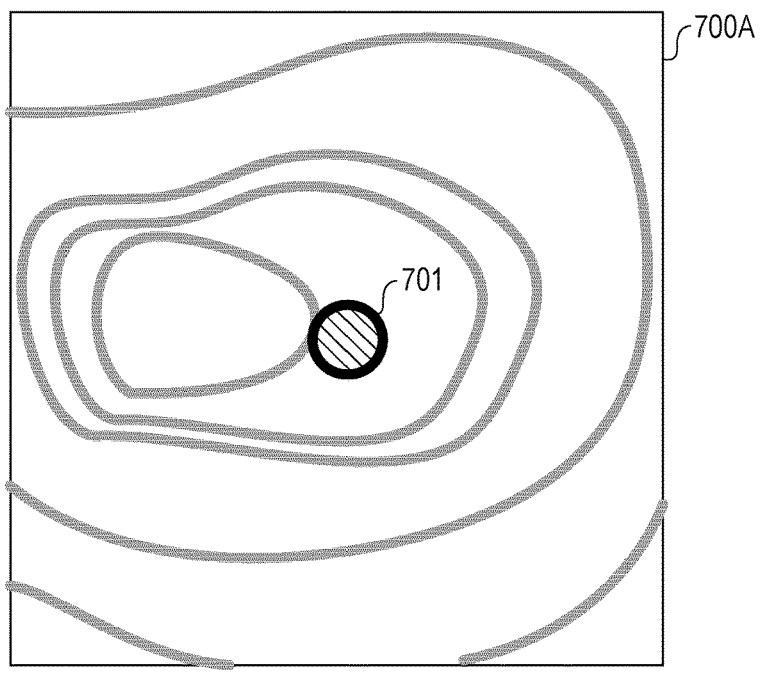
FIG. 7A is a diagram illustrating a display screen in which a danger marker is displayed in a virtual endoscopic image.
Figure 7B:
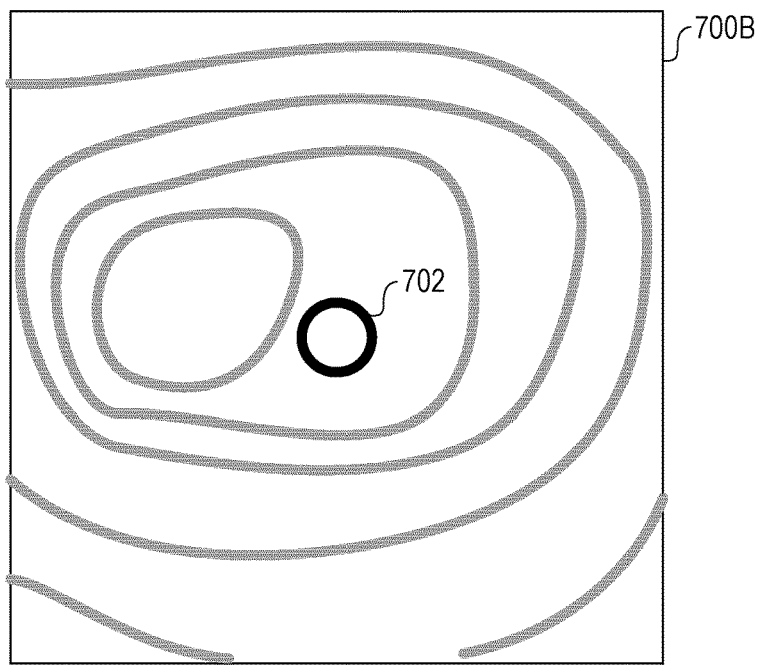
FIG. 7B is a diagram illustrating a display screen in which a lesion marker is displayed in a virtual endoscopic image.

At step S311, the CPU 201 of the medical-image processing apparatus 100 stores the point representing a position of the intersection of the inner wall model of the bronchial tube and the straight line into the RAM 202 or the external memory 211. The CPU 201 displays a lesion marker 702 (corresponding to an annotation) indicating that a lesion is present at the stored point representing the position of the intersection, for example, in white. For example, a virtual endoscopic image, like a screen example 700B shown in FIG. 7B, is displayed. In the screen example 700B, the lesion marker 702 is displayed such that the position of a lesion present outside the bronchial tube viewed from a viewpoint in the bronchial tube can be found.

At step S312, the CPU 201 of the medical-image processing apparatus 100 stores the point representing the position of the intersection of the inner wall model of the bronchial tube and the straight line into the RAM 202 or the external memory 211. The CPU 201 displays a danger marker 701, at the stored point representing the position of the intersection, indicating that a blood vessel is present between the viewpoint and the lesion, so that it is dangerous. For example, the lesion marker 702 is displayed in red, which is a color different from the color of a normal lesion marker. For example, a virtual endoscopic image, like a screen example 700A shown in FIG. 7A, is displayed. In the screen example 700A, the danger marker 701 indicating the position of the lesion and that inserting a needle from the position of the present viewpoint has a danger because of the presence of a blood vessel is displayed. This has the advantage of allowing the user to find the position of a lesion present outside the bronchial tube at a glance and to find out that a blood vessel is present, so that inserting a needle from the position of the viewpoint has a danger because of the presence of a blood vessel. This allows the user to take a suitable action, such as inserting the needle into the lesion from another viewpoint.

The present disclosure has the advantage of providing a system for determining whether a blood vessel is present outside a tubular structure.

Modification 1

In the above embodiment, when a blood vessel is present between the viewpoint and the lesion as shown in FIG. 7B, the display 210 displays the danger marker 701 at the position of the lesion viewed from the viewpoint. Alternatively, not the method of changing the color of the marker but another method can be employed which can notify the user that a blood vessel is present between the viewpoint and the lesion and that inserting a needle into the lesion from the position of the viewpoint would pose a danger, such as changing the blinking speed of the marker or displaying a pop-up screen on a virtual endoscopic image.

Figure 9:
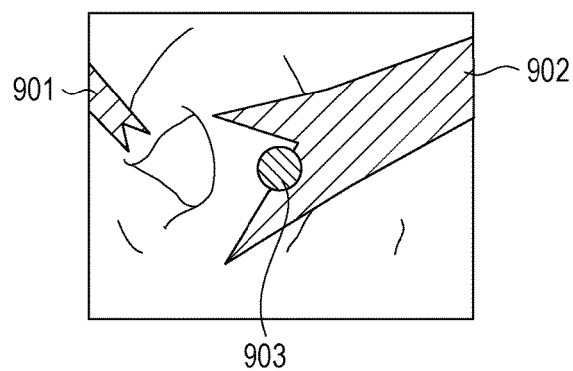
FIG. 9 is a diagram illustrating a display example of a two-dimensional image on a display.

In the above embodiment, the display 210 displays a marker indicating the position of the lesion. This is given for mere illustration, for example, an image of a blood vessel outside a tubular structure can be displayed, as shown in FIG. 9. In other words, in a two-dimensional image of the inner wall of a tubular structure based on the position of the viewpoint, a region that is determined to have a blood vessel outside the tubular structure may be displayed in a different manner from the other region. The CPU 201 controls the video controller 206 to display the two-dimensional image generated at step S308 on the display 210. In the display example of the two-dimensional image on the display 210, a region 901 and a region 902 are continuous parts of a body that are determined to have a blood vessel outside the tubular structure. The regions 901 and 902 are assigned a color different from that of a region determined not to have a blood vessel outside the tubular structure. A marker 903 is displayed at the position of the legion, or the target, projected onto the two-dimensional image. The doctor inserts a needle into the position indicated by the marker 903. In the example of FIG. 9, the position indicated by the marker 903 is in the region 902, and therefore inserting a needle into the position of the marker 903 may have the danger of inserting the needle into a blood vessel in the region 902. In this modification, the explicit display of the region 902 allows the doctor to visually recognize that a blood vessel is present in the needle insertion direction. Thus, the doctor can take appropriate measures, such as pushing up the inner wall, moving the blood vessel, and then inserting a needle.

Figure 10:
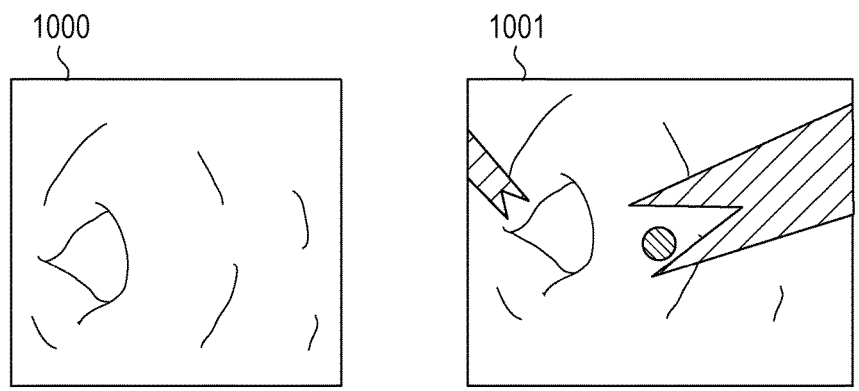
FIG. 10 is a diagram illustrating a display example of an endoscopic image and a two-dimensional image on a display.

Another display example is shown in FIG. 10. For example, if an endoscopic image captured by an endoscope (a device used to look inside a body cavity or organ) inserted in a bronchial tube (a tubular structure) can be acquired directly or indirectly, a two-dimensional image 1001 of an inner wall model viewed from a set viewpoint and an endoscopic image 1000 of the inner wall model may be displayed side by side, as shown in FIG. 10. This allows the doctor to determine the position and insertion direction of the needle while observing the image of the inner wall of the bronchial tube. Further, this allows the doctor to determine whether a blood vessel is present at the position and in the direction by observing the two-dimensional image of the inner wall of the bronchial tube taken based on the position of the viewpoint. The two-dimensional image of the inner wall of the bronchial tube taken based on the position of the viewpoint and the endoscopic image may be selectively displayed. The selection of the display image can be performed by the user operating the input controller 205.

Modification 2

In the above embodiment, it is determined whether a blood vessel is present on a straight line connecting the designated position of the lesion and the position of the starting point. In some embodiments, a three-dimensional region of the lesion is determined based on the designated position of the lesion, and it is determined whether a blood vessel is present on a plurality of straight lines connecting the outer periphery of the region and the starting point. If at least one blood vessel is present on one of the straight lines, it is determined that a blood vessel is present. A plurality of straight lines may be drawn from points on the outer periphery of the region containing the starting point to the position of the lesion, and if it is determined that a blood vessel is present on at least one of the straight lines, it is determined that a blood vessel is present.

In another aspect, the CPU 201 first selects an unselected target vector, as a selection target vector, among a target vector group (starting from the above viewpoint) with a length of D whose inner product with a vector extending from the present viewpoint position in the direction of the viewpoint (which can be changed by the user operation using the input controller 205) is 0 or greater and 1 or less (the starting point is the position of the viewpoint). The CPU 201 then creates a profile curve in which the CT values corresponding to the individual voxels from the starting point to the ending point of the selection target vector. The target vector group may be a set of vectors extending from the present viewpoint position in directions in the field of view.

If a plurality of profile curves is acquired, the CPU 201 determines whether determination of the presence of a blood vessel is performed on all the profile curves on the plurality of straight lines (the target vector group). The CPU 201 repeats the process from step S305 to step S310 in FIG. 3 until the determination of the presence of a blood vessel is completed on all of the straight lines (the target vector group).

Modification 3

In the above embodiment, the starting point is set at a given point. Alternatively, the determination of the presence of a blood vessel may be performed while the viewpoint position is being changed according to user operation. For example, subsequent to step S311 or step S312, the CPU 201 determines whether the user has input an instruction to move the viewpoint position by operating the input controller 205. If the result of determination is that an instruction to move the position of the viewpoint is input, the CPU 201 changes the position of the viewpoint according to the user operation and repeats the process from step S302 to step 312. If an instruction to move the position of the viewpoint is not input, the CPU 201 waits in a state in which the process at step S311 or step S312 is completed. The position of the viewpoint is moved in one direction or the other direction on a curve corresponding to the core axis of the bronchial tube in the inner wall model. The operating procedure and method for moving the viewpoint can be changed in various ways and are not limited to specific operating procedure and method.

Modification 4

The process shown in FIG. 3 can be performed when the position of the present viewpoint moves from the position of the target to a position within a threshold. If the position P of the endoscope at which the operation of inserting a needle, such as "inserting a needle from position P", is predetermined, the process in FIG. 3 can be performed when the position of the present viewpoint comes close to a position within a threshold from the position P.

Second Embodiment

In the first embodiment, a profile curve, which is a graph in which CT values corresponding to voxels on a straight line starting from the position of the starting point designated at step S302 and ending at the position of the lesion designated at step S303 are placed in sequence, is obtained, and whether a blood vessel close to the wall of the bronchial tube is present is determined based on the shape of the profile curve.

In this embodiment, a profile curve, which is a graph in which CT values corresponding to voxels on a straight line starting from the position of the starting point designated at step S302 and ending at the position of the lesion designated at step S303 are placed in sequence, is obtained, and whether a blood vessel close to the wall of the bronchial tube is present is determined based on the kurtosis (sharpness of the peak of a frequency-distribution curve corresponding to distribution information) of the profile curve.

In other words, the first embodiment performs the process according to the flowchart in FIG. 3, while this embodiment performs the process according to the flowchart in FIG. 8. The hardware configuration, functional configuration, and screen examples of the medical-image processing apparatus 100 are the same as those of the first embodiment, and descriptions thereof will be omitted.

The flowchart in FIG. 8 will be described.

Descriptions of the process from Step S801 to step S804 will be omitted because the process is the same as the process from step S301 to step S304 of the first embodiment in FIG. 3.

At step S805, the CPU 201 of the medical-image processing apparatus 100 obtains the kurtosis of the profile curve acquired at step S804. The calculation of the kurtosis of the profile curve uses CT values contained in the profile curve. Since a process for obtaining the kurtosis of the data is well known, a description thereof will be omitted.

At step S806, the CPU 201 of the medical-image processing apparatus 100 determines whether a blood vessel is present on the straight line based on the kurtosis obtained at step S805. If it is determined that a blood vessel is present on the straight line, the process goes to step S808; otherwise, the process goes to step S807.

Specifically, the determination of whether a blood vessel is present on the straight line using the kurtosis will be described. The CPU 201 determines whether the kurtosis obtained at step S805 is greater than or equal to a threshold. If the result of determination is that the kurtosis is greater than or equal to the threshold, the CPU 201 determines that a blood vessel close to the wall of the bronchial tube is not present between the starting point and the ending point of the selected straight line. If the kurtosis is less than the threshold, the CPU 201 determines that a blood vessel close to the wall of the bronchial tube is present between the starting point and the ending point of the selected straight line.

If the inner wall of the bronchial tube is present but a blood vessel is not present between the starting point and the ending point of the selected straight line, the kurtosis is greater than or equal to the threshold because the profile curve peaks only at a position corresponding to the inner wall of the bronchial tube. In contrast, if the inner wall of the bronchial tube and a blood vessel are present next to each other between the starting point and the ending point of the selected straight line, a peak corresponding to the inner wall of the bronchial tube and a peak corresponding to the blood vessel appear next to each other, and thus the peak as a whole expands, so that the kurtosis is less than the threshold. Thus, this embodiment determines the presence of a blood vessel based on the kurtosis of the profile curve. The threshold may be either any predetermined value or a value set by the user by operating the input controller 205.

Descriptions of the process from step S807 to step S813 will be omitted because it is the same as the process from step S306 to step S312 of the first embodiment in FIG. 3.

That is the descriptions of the second embodiment shown in FIG. 8. According to the second embodiment, a profile curve, which is a graph in which CT values corresponding to voxels on a straight line starting from the position of the starting point designated at step S302 and ending at the position of the lesion designated at step S303 are placed in sequence, is obtained, and whether a blood vessel is present close to the wall of the bronchial tube can be determined based on the kurtosis of the profile curve.

Thus, the present disclosure has the advantageous effect of providing a system for determining whether a blood vessel is present outside a tubular structure.

Although this embodiment has been described using the profile curve of CT values as an example, any other method can be employed that allows the distribution of CT values on a straight line to be determined so that whether a blood vessel is present on a straight line can be determined. For example, whether a blood vessel is present close to the wall of a bronchial tube may be determined using a histogram indicating the frequency distribution of the CT values.

The present disclosure can be embodied as a system, apparatus, method, program, or storage medium. Specifically, the present disclosure can be applied to a system constituted of a plurality of devices or an apparatus constituted of a single device. The present disclosure includes providing software programs that implement the functions of the above embodiments to a system or apparatus directly or under remote control. The present disclosure also includes achieving the functions by reading and implementing the provided program codes with an information processing unit of the system or apparatus.

Accordingly, the program codes installed in the information processing unit to implement the functions of the present disclosure are also included in the present disclosure. In other words, the present disclosure includes computer programs themselves for implementing the functions of the present disclosure.

In this case, the present disclosure may be in the form of an object code, a program implemented by an interpreter, or script data provided to an OS that has the functions of the program.

Examples of storage media for providing a program are a flexible disc, a hard disk, an optical disk, a magneto-optical (MO) disk, a compact disc read-only memory (CD-ROM), a compact disk recordable (CD-R), a compact disk rewritable (CD-RW), magnetic tape, a non-volatile memory card, a read-only memory (ROM), and digital versatile disc (DVDs: DVD-ROM and DVD-R).

Another method for providing a program is connecting to a website in the Internet using a browser of a client computer and downloading the computer program of the present disclosure of a compressed file including an automated install function from the website to a recording medium such as a hard disk.

The program codes that constitute the program of the present disclosure can be implemented by dividing it into a plurality of files and downloading the individual files from different websites. In other words, the present disclosure further includes a WWW server through which program files for implementing the functions of the present disclosure are downloaded by a plurality of users.

In some embodiments, the program of the present disclosure is encrypted, is stored in a storage medium, such as a CD-ROM, and is distributed to users. A user who satisfies predetermined conditions is permitted to download key information for decrypting the program from a website via the Internet, to decrypt the encrypted program using the key information, and to install it in the information processing apparatus to execute the program.

The functions of the foregoing embodiments can be implemented by the information processing apparatus by executing the read. The functions of the embodiments can also be implemented by an OS or the like that is operating on the information processing apparatus by performing part or all of the actual processes according to an instruction of the program.

Furthermore, the program read from the storage medium is written to a function expansion board inserted into the information processing apparatus or to a memory provided in a function expansion unit connected to the information processing apparatus. Thereafter, a CPU or the like mounted on the function expansion board or the function expansion unit performs all or part of the actual process, so that the functions of the foregoing embodiments can be implemented.

The above embodiments are mere examples of the present disclosure and are not intended to limit the technical scope of the present disclosure. In other words, the present disclosure can be embodied in various forms without departing from the technical spirit or the main features thereof.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-Ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-248287, filed Dec. 21, 2015, and No. 2015-248983, Dec. 21, 2015, which are hereby incorporated by reference herein in their entirety.

What is claimed is:

1. An information processing apparatus comprising:
    an acquisition unit configured to acquire a three-dimensional image containing at least a tubular structure;
    a specification unit configured to specify a first point inside the tubular structure and specify a lesion outside the tubular structure in the three-dimensional image;
    a determination unit configured to determine whether a blood vessel is present in a region between the first point and the lesion based on signal values of voxels of the three-dimensional image in the region between the first point and the lesion;
    a generation unit configured to generate a two-dimensional image of the tubular structure viewed from the first point based on the three-dimensional image; and
    a display control unit configured to display information indicating a region of the lesion on the two-dimensional image to be distinguishable in a result of determining whether a blood vessel is present in the region.

2. The information processing apparatus according to claim 1, wherein the display control unit is configured to display the information indicating the region of the lesion on the two-dimensional image in different manners between a case in which a blood vessel is present between the first point and the lesion and a case in which no blood vessel is present between the first point and the lesion.

3. The information processing apparatus according to claim 1, wherein the display control unit is configured to display information indicating a region of the determined blood vessel on the two-dimensional image.

4. The information processing apparatus according to claim 1, further comprising a receiving unit configured to receive input of a user operation for specifying the lesion,
wherein the specification unit is configured to specify the lesion in the three-dimensional image based on the received input.

5. The information processing apparatus according to claim 1,
wherein the specification unit is configured to specify the first point in the three-dimensional image in correspondence with a position of an endoscope inserted in the tubular structure, and
wherein the display control unit is configured to display an endoscopic image acquired by the endoscope and the two-dimensional image.

6. The information processing apparatus according to claim 1, wherein the determination unit is configured to determine whether a blood vessel is present on a straight line passing through a second point in the lesion and the first point based on the signal values of the voxels on the straight line.

7. The information processing apparatus according to claim 6, wherein the determination unit is configured to generate a graph of signal values on the straight line and to determine whether a blood vessel is present between the first point and the second point.

8. The information processing apparatus according to claim 7, wherein the determination unit is configured to determine that a blood vessel is present when a section of signal values exceeding a threshold in the graph is larger than or equal to a predetermined threshold.

9. The information processing apparatus according to claim 7, wherein the determination unit is configured to determine that a blood vessel is present when kurtosis of a section of signal values exceeding a threshold in the graph is less than a predetermined threshold.

10. The information processing apparatus according to claim 7, further comprising a section specification unit configured to specify a section of the graph in which the signal values exceeds a threshold,
wherein the determination unit is configured to determine that a blood vessel is present on the straight line when the section specified by the section specification unit is longer than a predetermined length.

11. The information processing apparatus according to claim 7, further comprising a distribution-information acquisition unit configured to acquire distribution information indicating a distribution state of the signal values in the graph,
wherein the determination unit is configured to determine that no blood vessel is present on the straight line when the distribution information acquired by the distribution-information acquisition unit indicates that the signal values are biased by a predetermined value or more.

12. The information processing apparatus according to claim 1, wherein the determination unit is configured to generate a graph of signal values on at least one vector starting from the first point and passing through at least one of points in the lesion and to determine, based on the graph, whether a blood vessel is present in a region between the first point and the lesion.

13. The information processing apparatus according to claim 1, wherein the display control unit is configured to display a warning that a blood vessel is present in the region between the first point and the lesion when the determination unit determines that a blood vessel is present between the first point and the lesion.

14. The information processing apparatus according to claim 13, wherein the display control unit is configured to indicate whether a blood vessel is present in the region between the first point and the lesion by controlling a display form of annotation displayed on the two-dimensional image, wherein the annotation is the information indicating the region of the lesion.

15. The information processing apparatus according to claim 1, further comprising a moving unit configured to move the first point.

16. The information processing apparatus according to claim 1, wherein the tubular structure comprises a bronchial tube and a stomach.

17. The information processing apparatus according to claim 1, wherein the blood vessel is a blood vessel satisfying a predetermined condition.

18. An information processing apparatus comprising:
an acquisition unit configured to acquire a three-dimensional image containing at least a tubular structure;
a specification unit configured to specify a first point inside the tubular structure and a second point in a lesion outside the tubular structure in the three-dimensional image;
a determination unit configured to determine whether a blood vessel is present between the first point and the second point based on signal values of voxels on a straight line passing through the first point and the second point;
a generation unit configured to generate a two-dimensional image of the tubular structure viewed from the first point based on the three-dimensional image; and
a display control unit configured to display information indicating a region of the lesion and information indicating a region of the determined blood vessel on the two-dimensional image.

19. The information processing apparatus according to claim 18, wherein the blood vessel is a blood vessel satisfying a predetermined condition.

20. An information processing method for an information processing apparatus, the information processing method comprising:
acquiring a three-dimensional image containing at least a tubular structure;
specifying a first point inside the tubular structure and specifying a lesion outside the tubular structure in the three-dimensional image;
determining whether a blood vessel is present in a region between the first point and the lesion based on signal values of voxels of the three-dimensional image in the region between the first point and the lesion;
generating a two-dimensional image of the tubular structure viewed from the first point based on the three-dimensional image; and
displaying information indicating a region of the lesion on the two-dimensional image to be distinguishable in a result of determining whether a blood vessel is present in the region.

21. A non-transitory storage medium storing a program to cause a computer to perform an information processing method for an information processing apparatus, the information processing method comprising:
acquiring a three-dimensional image containing at least a tubular structure;
specifying a first point inside the tubular structure and specifying a lesion outside the tubular structure in the three-dimensional image;

determining whether a blood vessel is present in a region between the first point and the lesion based on signal values of voxels of the three-dimensional image in the region between the first point and the lesion;

generating a two-dimensional image of the tubular structure viewed from the first point based on the three-dimensional image; and displaying information indicating a region of the lesion on the two-dimensional image to be distinguishable in a result of determining whether a blood vessel is present in the region.

22. An information processing apparatus comprising:

an acquisition unit configured to acquire a three-dimensional image of an object;

a specification unit configured to specify a first position in the object and a second position of a lesion in the three-dimensional image;

a determination unit configured to determine whether a blood vessel satisfying a predetermined condition is present in a region between the first position and the second position based on signal values of voxels of the three-dimensional image in the region; and a display control unit configured to cause a display unit to display information relating to a result of determination.

23. The information processing apparatus according to claim 22, wherein the three-dimensional image contains at least a tubular structure, and the first position is a position in the tubular structure.

24. The information processing apparatus according to claim 23, wherein the lesion is present outside the tubular structure.

25. An information processing method for an information processing apparatus, the information processing method comprising:

acquiring a three-dimensional image of an object;

specifying a first position in the object and a second position of a lesion in the three-dimensional image;

determining whether a blood vessel satisfying a predetermined condition is present in a region between the first position and the second position based on signal values of voxels of the three-dimensional image in the region; and causing a display unit to display information relating to a result of determination.

* * * * *